US008232077B2

(12) United States Patent
Bukovsky et al.

(10) Patent No.: US 8,232,077 B2
(45) Date of Patent: Jul. 31, 2012

(54) OOCYTES DERIVED FROM OVARIAN CULTURE INITIALLY CONTAINING NO OOCYTES

(75) Inventors: Antonin Bukovsky, Knoxville, TN (US); Michael R. Caudle, Maryville, TN (US)

(73) Assignee: Ovacyte LLC, Gladwyne, PA (US)

( * ) Notice: Subject to any disclaimer, the term of this patent is extended or adjusted under 35 U.S.C. 154(b) by 0 days.

(21) Appl. No.: 11/473,910

(22) Filed: Jun. 23, 2006

(65) Prior Publication Data

US 2007/0010013 A1    Jan. 11, 2007

Related U.S. Application Data

(60) Provisional application No. 60/696,952, filed on Jul. 6, 2005.

(51) Int. Cl.
*C12P 21/04* (2006.01)
*C12N 15/00* (2006.01)
(52) U.S. Cl. ................... 435/70.3; 435/325
(58) Field of Classification Search ............... 800/24; 435/70.3, 325
See application file for complete search history.

(56) References Cited

OTHER PUBLICATIONS

Alper, et al, Human Reproduction, 16(4): 617-619, 2001.*
Borini et al, Reproductive BioMedicine Online, 10(5): 6653-668, 2005.*
Bukovsky et al, Reproductive Biology and Endocrinology, 3: 17, 2005.*
Gregoire, et al, Clinical Cancer Research, 7: 4280-4287, 2001.*
Johnson et al, Nature, 428: 145-150, 2004.*
Siemens et al, Journal of Cellular Physiology, 134:347-356, 1988.*
Bukovsky et al, Expert Opin Biol Ther, 6(4): 341-365, 2006.*
Powell and et al, Nature, 11(9): 911, 2005.*
Kayisli et al, Current Opinion in Obstetrics and Gynecology, 18: 338-343, 2006.*
Telfer, Reproductive Biology and Endocrinology, 2: 24-25.*
Oktay et al, (Fertil Steril, 67(3): 481-6, 1997.*
Wright et al, (Dev Genet, 18: 173-179, 1996.*
Kinugawa et al, (Tohoku J Exp Med, 190: 231-238, 2000.*
Parrot et al, Biology of Reproduction, 62: 1600-1609, 2000.*
Castrillon et al, (PNAS, 97-17: 9585-9590, 2000.*
Rienzi et al (Human Reproduction Update, 00(0): 1-12, 2010).*
Malcov et al (Fertility and Sterility, 91(3): 932.e3-e6, 2009).*
Ebner (Journal of Mammalian Ova Research, 26(1): 18-25, 2009).*
Cheng et al (Reproduction, Fertility and Development, 22: 1167-1174, 2010).*
Patrizio et al (RBM Online, 15(3): 346-353, 2007).*
Deger et al, (Cancer Genet Cytogenet 96:166-173, 1997 (abstract)].*
Rosenbusch et al (Fertil Steril, 90: 49-55, 2008).*
Balakier et al (human reproduction, 2002 17(9) 2394-2401).*
Virant-Klun et al [Stem Cells and Development, Original Research Report, p. 1-43, 2007].*
Bergh et al (Hum Reprod, 8(4):519-24, 1993 (Abstract provided).*
McNatty (J Clin Endocrinol Metab. 49(5):687-99,, 1979, Abstract provided).*
Gosden, RG, Germline stem cells in the postnatal ovary: is the ovary more like a testis?, Human Reproduction Update, 10(3):193-195 (2004).
Picton, HM, and Gosden, RG, In vitro growth of human primordial follicles from frozen-banked ovarian tissue, Molecular and Cellular Endocrinology, 166:27-35 (2000).
Okamura, H, et al, What we have learned from isolated cells from human ovary?, Molecular and Cellular Endocrinology, 202:37-45 (2003).
Auersperg, N et al, Human ovarian surface epithelium in primary culture, In Vitro, 20(10):743-755 (1984).
Nicosia, SV et al, Isolation and ultrastructure of rabbit ovarian mesothelium (surface epithelium), Int. J. Gynecol. Pathol., 3:348-360 (1984).
Nicosia, SV et al, Growth characteristics of rabbit ovarian mesothelial (surface epithelial) cells, Int. J. Gynecol. Pathol., 4:58-74 (1985).
Kruk, PA et al, Reciprocal interactions between human ovarian surface epithelial cells and adjacent extracellular matrix, Exp. Cell Res., 215:97-108 (1994).
Bukovsky, A et al, Immunohistochemical studies of the adult human ovary: possible contribution of immune . . . , Am. J. Reprod. Immunol., 33:323-340 (1995).
Karlan, BY et al, Secreted ovarian stromal substance inhibits ovarian epithelial cell proliferation, Gynecologic Oncology, 59:67-74 (1995).
Dyck, HG et al, Autonomy of the epithelial phenotype in human ovarian surface epithelium: changes with neoplastic . . . , Int. J. Cancer, 69:429-436 (1996).
Auersperg, N et al, E-cadherin induces mesenchymal-to-epithelial transition in human ovarian surface epithelium, Proc. Natl. Acad. Sci., 96:6249-6254 (1999).
Auersperg, N et al, Ovarian surface epithelium: biology, endocrinology, and pathology, Endocrine Reviews, 22(2):255-288 (2001).
Parrott, JA et al, Expression and actions of both the follicle stimulating hormone receptor and the luteinizing hormone . . . , Mol. Cell Endocrinol., 172:213-222 (2001).
Choi, KC et al, Follicle-stimulating hormone activates mitogen-activated protein kinase in preneoplastic and neoplastic . . . , J. Clin. Endocrinol. Metal., 87:2245-2253 (2002).
Liu, J et al, In vitro parthenogenetic development of mouse oocytes following reciprocal transfer of the chromosome spindle . . . , Biol. Reprod., 68:186-189 (2003).

(Continued)

*Primary Examiner* — Gerald Leffers, Jr.
*Assistant Examiner* — Magdalene Sgagias
(74) *Attorney, Agent, or Firm* — Howard Eisenberg, Esq.

(57) ABSTRACT

Ovarian germ-line-competent embryonic stem cells (GLC-ESC) are cultured, either in the presence or absence of a compound having estrogenic activity. The GLC-ESC are either collected prior to specific commitment or are permitted to remain in the culture medium for a time sufficient to develop into oocytes, and the oocytes may be fertilized by adding sperm to the culture medium. The fertilized oocytes may be permitted to develop into embryos, which may be transferred into the uterus of an adult human female or frozen for later use. The invention provides a method for obtaining by in vitro fertilization an embryo that is genetically related to a human female who is not producing oocytes.

6 Claims, No Drawings

OTHER PUBLICATIONS

Gubbay, O et al, Anti-inflammatory and proliferative responses in human and ovine ovarian surface epithelial cells, Reproduction, 128:607-614 (2004).

Johnson, J et al, Germline stem cells and follicular renewal in the postnatal mammalian ovary, Nature, 428:145-150 (2004).

Piek, JMJ et al, Cultures of ovarian surface epithelium from women with and without a hereditary predisposition to develop . . . , Gynecol. Oncology, 92:819-826 (2004).

Woo, MMM et al, Oviductal glycoprotein, a new differentiation-based indicator present in early ovarian epithelial neoplasia . . . , Gynecol. Oncology, 93:315-319 (2004).

Bukovsky Antonin et al, Origin of germ cells and formation of new primary follicles in adult human ovaries, Reprod. Biol. and Endocrinol., 2:20-49 (2004) (internet version).

* cited by examiner

OOCYTES DERIVED FROM OVARIAN CULTURE INITIALLY CONTAINING NO OOCYTES

This application claims priority from U.S. Provisional Patent Application Ser. No. 60/696,952, filed on Jul. 6, 2005, which provisional patent application is incorporated in its entirety into this application by reference.

FIELD OF THE INVENTION

This invention pertains to the field of culturing cells and in particular to the field of culturing human ovarian cells and to the field of utilizing oocytes cultured from these cells for fertilization and implantation into a human uterus.

BACKGROUND OF THE INVENTION

The belief that all primary follicles in adult mammalian females were formed during the fetal period has persisted for over fifty years, primarily due to the diminution in the number of primary follicles that occurs with age. Recent studies, however, have brought this belief into question.

Bukovsky, et al, Am. J. Reprod. Immunol., 33:323-340 (1995), reported that the ovarian surface epithelium (OSE) is a source of germ cells in adult human females. Bukovsky, et al, Reprod. Biol. Endocrinol., 2:20 (2004) reported that new primary follicles are formed by assembly of oocytes with nests of primitive granulosa cells in the human ovarian cortex during adulthood.

These studies have suggested that the hypothesis that all primary follicles in adult human females were formed during the fetal period is incorrect. Rather, these studies indicate that primary follicles that were formed during the fetal period may persist for some time, perhaps through childhood, and then starting with menarche, new cohorts of primary follicles replace the fetal follicles that undergo atresia. Moreover, it is suggested that during each successive menstrual cycle until about the age of 38, fresh follicles are produced that replace older follicles. At about the age of 38±2 years, formation of new primary follicles ceases, possibly due to the onset of immune senescence (certain immune system-related cells appear to be required for the formation of new germ cells from the OSE), and the aging follicles accumulate genetic alterations until exhausted at the onset of natural menopause.

In recent years, women in developed countries have an increased tendency to delay having a first child. Reasons for waiting to start a family include the desire to wait until the family has financial security and the desire of women to commit to their marriages and to their careers before focusing their energy on children. According to the National Center for Health Statistics, the birth rate for women aged 40-45 years rose 20% between 1990 and 1995, and increased 74% during 1981-95. The rising birth rate along with the increasing number of women in this age group means that there were more babies born in 1995 to mothers in their 40s than in any year since 1966.

A significant problem that occurs due to delayed parenting is that often women over the age of 40 have a greatly decreased chance of becoming pregnant. Much of this difficulty stems from a decrease in the availability of oocytes that are available for fertilization. Additionally, women below the age of 40 that have premature ovarian failure are unable to become pregnant due to the lack of production of oocytes.

A woman who desires to become pregnant but who does not produce her own oocytes may elect to undergo a procedure referred to as in-vitro fertilization (IVF) in which eggs donated from another woman are fertilized in vitro and then one or two of the resultant developing embryos are implanted into her uterus. Of course, the resultant child from this procedure will be genetically unrelated to the woman undergoing this procedure. At the present time, there are no procedures available by which a woman who does not produce oocytes is able to produce a child who is genetically related to her.

An important need exists for the development of methodologies that will permit a woman who does not produce oocytes that have the potential to develop into an offspring who is genetically related to her.

DESCRIPTION OF THE INVENTION

It has been unexpectedly discovered that that cultures of adult ovarian stem cells are capable of differentiating into oocytes and mature eggs. These oocytes may be fertilized in vitro and then implanted into the uterus of an adult human female. The fertilized oocytes are capable of further developing into human embryos.

In one embodiment, the invention is a method for obtaining human oocytes from culture. According to this embodiment of the invention germ-line-competent embryonic stem cells (GLC-ESC cells), which are ovarian surface epithelial (OSE) cells or activated mesenchymal tunica albuginea (TA) cells, are cultured for a time sufficient to produce oocytes in the culture medium. Activated mesenchymal TA cells are those that express cytokeratin. The oocytes thus produced may be used for the autologous or allogeneic treatment of ovarian infertility. For that purpose, the oocytes may be fertilized in vitro and then permitted to develop into embryos, which may be collected and utilized, such as for intrauterine implantation, for the treatment of ovarian sterility. If desired, the oocytes may be frozen, before or after fertilization, and utilized at some time in the future.

In another embodiment, the invention is a method for obtaining fertilized oocytes. According to this embodiment of the invention germ-line-competent embryonic stem cells (GLC-ESC cells), which are ovarian surface epithelial (OSE) cells or activated mesenchymal tunica albuginea (TA) cells, are cultured for a time sufficient to produce oocytes in the culture medium. The oocytes are fertilized in vitro and then permitted to develop into embryos, which may be collected and utilized, either fresh or frozen and thawed, for intrauterine implantation for the treatment of ovarian sterility.

In another embodiment, the invention is a method for in-vitro fertilization. According to this embodiment of the invention, germ-line-competent embryonic stem cells (GLC-ESC cells), which are ovarian surface epithelial (OSE) cells or activated mesenchymal tunica albuginea (TA) cells, are cultured for a time sufficient to produce oocytes in the culture medium. The oocytes are fertilized in vitro and then permitted to develop into embryos, which may be collected and transferred, either fresh or following freezing and thawing, into the uterus of a human adult female.

In another embodiment, the invention is a method for producing a human embryo that is genetically related to a donor female human. According to this embodiment of the invention, germ-line-competent embryonic stem cells (GLC-ESC cells), which are ovarian surface epithelial (OSE) cells or activated mesenchymal tunica albuginea (TA) cells, are obtained from the ovary of an adult female human. The cells are cultured for a time sufficient to produce oocytes in the culture medium. The oocytes are fertilized in vitro and then permitted to develop into embryos, which embryo is genetically related to the female human. The embryo thus obtained may be collected and transferred, either fresh or following freezing and thawing, into the uterus of the female human.

The culture medium for this embodiment of the invention may or may not contain a chemical compound that has estrogenic activity. One example of such a chemical compound is phenol red. GLC-ESC cells that are cultured in accordance with the method of the invention in the presence of a chemical compound, such as phenol red, that has estrogenic activity, typically produce oocytes starting at about 4 to 6 days after initiation of the culture. It is conceived that an effect of estrogen is to drive the GLC-ESC cells to develop into oocytes.

Alternatively, the culture medium may be devoid of a chemical compound that has estrogenic activity prior to placing cells in the medium. In this case, it has been surprisingly discovered that oocytes will also develop. Such development of oocytes, however, occurs later in time than that which occurs in culture medium containing a source of estrogenic activity. Typically, oocytes are detected in culture medium lacking a chemical compound after 10 to 12 days in culture. Although the inventors do not intend to be bound by theory, it is conceived that estrogen may be required for the development of oocytes from GLC-ESC cells and that, in the case of a culture medium free of estrogenic activity, such estrogenic activity may come from cells, such as fibroblasts, that often accompany the GLC-ESC cells in culture.

The GLC-ESC cells may be obtained by any means by which such cells are capable of being obtained. The cells preferably are removed, such as by scraping, from the surface of an ovary within a subject, such as during a surgical or laparoscopic procedure or from a biopsy sample of an ovary. The cells may also be removed, such as by scraping, from the surface of an ovary that has been surgically removed from a patient. Suitable OSE cells may also be obtained, not only from the ovarian surface, but also from OSE crypts within the ovary, for example by scraping the stroma of dissected ovaries or by trypsinization of a small ovarian biopsy.

The GLC-ESC culture may be a primary or secondary culture. Primary cultures of ovarian tissue often include various types of cells, including granulosa cells, epithelial cells, and fibroblasts. Secondary cultures lack granulosa cells.

The ovaries from which the GLC-ESC cells are obtained may be from an adult woman of any age. The woman may be premenopausal, postmenopausal, or anovulatory. It has been discovered that OSE cells cover the ovarian surface more thoroughly in ovaries that are postmenopausal or anovulatory. Therefore, because of the relative ease of procuring suitable GLC-ESC cells, such ovaries are preferred. However, if present, GLC-ESC cells from any ovary may be utilized.

In culture, in addition to their characteristic morphology, the oocytes may also be identified by alkaline phosphatase activity. Zona pellucida (ZP) proteins and some ZP antigens, such as PS1 meiotically expressed carbohydrate antigen and heat-solubilized porcine zona (HSPZ) proteins, are more specific markers. The oocytes may also express CK18, a marker of the Balbiani body. Furthermore, oocytes also express the intermediate filament vimentin, a protein which plays an important role in the maturation and fertilization of eggs.

The invention is further illustrated in the following non-limiting examples.

EXAMPLE 1

Production of Oocytes from Ovarian Culture

EXAMPLE 1a

Collection of GLC-ESC Cells

All chemicals and consumables, except where specified otherwise, were purchased from Sigma Chemical Co., St. Louis, Mo. Cultured cells were collected from ovaries associated with fresh hysterectomylbilateral salpingooophorectomy specimens. The surgery was performed for medical indications, including chronic pelvic pain, uterine fibroids, and/or uterine bleeding (severe dysmenorrhea) not responding to conservative treatment. The surface of intact ovaries was gently scraped in an aseptic laminar flow hood with a sterile stainless steel surgery knife blade No. 21 (Becton Dickinson, AcuteCare, Franklin Lakes, N.J.). This procedure was selected with an intention include OSE and some adjacent TA mesenchymal cells.

EXAMPLE 1b

Culture of GLC-ESC Cells

The cells of Example 1a were collected into sterile petri dishes containing tissue culture medium supplemented with heat inactivated 20% fetal bovine serum (FBS; Gibco/BRL, Grand Island, N.Y.) and antibiotics (50 µg/ml gentamycin, 100 U/ml penicillin, and 100 µg/ml streptomycin). The tissue culture media utilized was either Dulbecco's Modified Eagle Medium/Ham's F12, phenol red free (DMEM/F12;without estrogenic stimuli) or Dulbecco's Modified Eagle's Medium containing 25 mM HEPES, 4500 mg/L glucose, and phenol red (DMEM-HG; with estrogenic stimuli). There was no other treatment imposed during the culture.

The cells were spun down (1000×g, 5 min, 24° C.), diluted in 0.75-1.5 ml of supplemented media, seeded in either 3 or 6 wells of a 24-well plate (250-350 µl per well) (Fisher Scientific, Pittsburgh, Pa.), and cultured in an humidified atmosphere with 5% CO2 at 37° C. The number of wells was chosen by the size of ovaries. Cells collected from small ovaries were seeded into 3 wells, and from larger ovaries into six wells. All ovaries involved in the experiment were anovulatory, as no corpora lutea were detected. The culture medium was changed once after 24 hours. This left only adherent (viable) cells in culture, and eliminated non-adherent cells and the majority of contaminating erythrocytes. The cell cultures were monitored daily by phase contrast microscopy and live cells evaluated by immunohistochemistry after 5-6 days from the initial seeding. Viability of cells was apparent from their active movement, changes in shape, and movement of their nuclei. The number of adherent cells in a single well of 24-well plate ranged between ~100 to 1000 during the late culture period (day 5 or 6).

EXAMPLE 1c

Immunohistochemistry

The medium was aspirated from wells of the 24-well plate, and cells were allowed to dry under a fan before placing them in a ventilated hood overnight. The bottoms of the wells were dried in the upright position and found macroscopically dry within a few seconds. The cells were fixed with 96% ethanol for 5 minutes, allowed to dry again, and incubated overnight (4° C.) with primary antibodies against zona pellucida (ZP) proteins: rabbit-anti heat solubilized porcine zona (HSPZ, 1:20) or mouse monoclonal PS1 antibody recognizing meiotically expressed ZP carbohydrate antigen diluted 1:10 in phosphate buffered solution (PBS), pH 7.22. We also used mouse-anti human CK18, clone CY90, Sigma (diluted 1:50), mouse antihuman CK5,6,8,17, clone MNF116 (DAKO Corporation, Carpinteria, Calif.) (diluted 1:50), and mouse anti-human vimentin, clone V9 (DAKO Corporation) (diluted 1:50). As a control, an HLA-DR antibody which does not react with OSE cells, was used. We used an HLA-DR antibody not reacting with fibroblast, granulosa, epithelial, germ or oocyte cell types, in order to identify activated tissue macrophages, but did not find any such cells in day 5 or 6 cultures. After several washes in PBS (room temperature), the cells were incubated with peroxidase labeled corresponding secondary antibodies—goat anti-rabbit IgG, pre-absorbed with human serum (Jackson Immunoresearch, West Grove, Pa.), diluted 1:50; or swine anti-mouse IgG, diluted 1:50 and absorbed with rat kidney homogenate to remove background. After additional washes in PBS (room temperature), the bound antibodies were visualized by diaminobenzidine substrate, but without hematoxylin counterstain, covered with PBS, and images captured as described below. The cells stained for CK18 or ZP were processed further for dual color immunohistochemistry to identify co-expression of other proteins, and visualized with blue chromogen substrate. Finally, the washed cells were covered with PBS containing 0.01% azide as a preservative.

EXAMPLE 1d

Image Processing

Two independent observers evaluated the live cells by phase contrast and subsequent immunohistochemistry using an inverted microscope (NIKON, Nikon Inc., Instrument Division, Garden City, N.Y.) equipped with a DEI-470 CCD Video Camera System (Optronics Engineering, Goleta, Calif.) with detail enhancement. The video images were captured by CG-7 color frame grabber (Scion Corporation, Frederick, Md.) supported by Scion Image public software developed at the National Institutes of Health (Wayne Rasband, NIH, Bethesda, Md.), and ported to Windows XP, 2002 release (Microsoft Corporation, Redmond, Wash.). To obtain figure panels, the captured video images were copied into Microsoft® Power-Point® 97 SR-2 (Microsoft Corporation). Each image (including controls) was further copied into Microsoft Photo Editor 3.0 (Microsoft Corporation), and blue saturation adjusted (brightness 70, contrast 70, gamma 0.30). In total, more than 100 images were captured and stored.

EXAMPLE 1e

40 Year Old Female

Ovarian cells were collected from the ovary of a 40-year old woman as described in Example 1a and cultured in DMEM-HG supplemented with 20% FBS and antibiotics as described in Example 1b. Initial examination of the cells at time of culture showed a uniform pattern of epithelial type cells, while no other cell types, including mesenchymal and granulosa cells, were present.

Phase contrast microscopy, as described in Example 1d, revealed large cells exhibiting an oocyte phenotype in the OSE culture after 5 days. These cells reached 180 µm in diameter and showed a centrally located 40 µm nucleus with nucleolus, and perinuclear accumulation of organelles.

Immunohistochemical staining of the cells, as described in Example 1c, showed diffuse CK immunoexpression with a preserved accumulation of staining around the cell nucleus. The perinuclear space also exhibited enhanced staining for ZP proteins in the same cell. Control immunohistochemical staining using the anti-HLA antibody showed no reaction. Clusters of OSE cells with perinuclear ZP expression and differentiation into large cells resembling oocytes was also observed.

EXAMPLE 1f

39 Year Old Woman

Ovarian tissue was collected from a 39 year-old woman as described in Example 1a. Prior to culture, a portion of the collected ovarian tissue was passed through a cell strainer in order to ensure that mostly single cells, and not cell sheets, were seeded in the culture medium. Unstrained and strained cells were cultured, as described in Example 1b, in medium containing phenol red (DMEM-HG; with estrogenic stimuli) or in medium lacking phenol red (DMEM/F12;without estrogenic stimuli).

Except for the occasional mesenchymal cells of the fibroblast phenotype, there was no evidence of cell commitment until day 4 of culture. On day 5 the cells collected from the ovarian surface and strained did not progress beyond the state found on day 3, and no oocytes were detected regardless of the presence or absence of phenol red.

However, many cells with an oocyte phenotype were found in mixed cultures, unstrained cells, in cultures containing phenol red. They showed moderate (100 µm) size without zona pellucida and were accompanied by fibroblasts. Larger oocytes (120 µm) accompanied by fibroblasts showed a developing zona layer.

The reason that oocytes were not found on day 5 culture (last day of culture) of cells that had been passed through a cell strainer was not determined. It is conceived that the passage of the cells through the cell strainer prevented the passage of OSE cell sheets. Because the culture was not continued beyond day 5, it is also conceived that it may require additional time for the development of oocytes from cultures lacking sheets of OSE cells.

Similarly, cells cultured without estrogenic stimuli did not show oocyte development in day 5 culture. However, 12 day cultures of ovarian cells showed the presence of oocytes. It is conceived that natural estrogenic stimulation is provided by fibroblasts that accompany OSE cells in the culture.

EXAMPLE 1g

36 Year Old Woman

Ovarian tissue was collected from a 36 year-old woman. Immunohistochemistry of the tissue showed the presence of CK+OSE cells and no primary follicles. New oocytes developed in the culture.

EXAMPLE 1h

50 Year Old Woman

Ovarian tissue was collected from a 50 year-old woman. Immunohistochemistry of the tissue showed no OSE or primary follicles. No new oocytes developed in the culture.

EXAMPLE 1i

39 Year Old Woman

Ovarian tissue was collected from a 39 year-old woman. Immunohistochemistry of the tissue showed the presence of OSE cells and CK+mesenchymal cells in the TA, and a lack of primary follicles. New oocytes developed in the culture.

EXAMPLE 1j

55 Year Old Woman

Ovarian tissue was collected from a 55 year-old woman. Immunohistochemistry of the tissue showed no primary follicles, but CK+TA and OSE at the ovarian surface. The ovaries also showed cortical epithelial crypts with CK+OSE. Culture of this tissue produced new oocytes.

EXAMPLE 1k

67 Year Old Woman

Ovarian tissue was collected from a 67 year-old woman. This woman was the most advanced age studied. Culture of the tissue as described in Example 2 produced new oocytes. In addition, tissue from the culture was secondarily cultured. The secondary culture contained only epithelial clusters and fibroblasts and had no granulosa cells, which were present in the primary culture. The secondary culture of the atrophic ovarian tissue of this woman produced new oocytes.

EXAMPLE 2

Fertilization of Cultured Ovarian Stem Cells Derived from Infertile Woman with Premature Ovarian Failure

EXAMPLE 2a

Collection of Ovarian Tissue

Ovarian tissue was collected during diagnostic laparoscopic examination under general anesthesia from three infertile women, ages 30 (Patient 1), 38 (Patient 2), and 40 (Patient 3) years old, with premature ovarian failure (POF). First the surface of each ovary was gently scrapped with laparoscopic scissors and cells collected by washing branches of the scissors in tissue culture medium. Additional cells were similarly collected by laparoscopic brushes. Next each ovary was washed with 10 ml saline solution, and the fluid was collected from the pouch of Douglas. Finally, a small biopsy (15×5 mm) was collected from each ovary and the biopsy site was closed with a single suture. Examination of the ovaries from the three women revealed the absence of oocytes.

EXAMPLE 2b

Culture of Ovarian Tissue

All chemicals were purchased from Sigma, St. Louis, Mo., USA, except where indicated otherwise. For cultures, Dulbecco's Modified Eagle's Medium Nutrient Mixture/F-12 Ham Medium (1:1) with L-glutamine, 15 mM HEPES, and phenol red was used. The medium was supplemented with sodium bicarbonate—3.7 g/L, antibiotics—50 µg/ml gentamycin, 100 U/ml penicillin, and 100 µg/ml streptomycin (DMEM/F12), and with 20% comprehensively heat inactivated human serum (HuS) of the corresponding patient.

For this purpose, 30 ml of venous blood was collected into sterile tubes and allowed to coagulate at room temperature. After coagulation the blood sample was spun down for 10 minutes at 3000×g, serum pipetted into new tubes and heat-inactivated for 60 minutes in the 59° C. water bath. The serum after such extensive heat inactivation was spun down again to sediment additionally coagulated proteins, and noncoagulated proportion pipetted into new tubes and stored at −20° C. until utilization.

Half of each ovarian biopsy was placed in a sterile Petri dish with DMEM/F12 medium, and a sterile surgery blade was used to scratch the cells from all surfaces. In addition, the tissue in medium was minced with the blade into small pieces. Next the cells were collected by passing the medium with cells and tissue remnants through the 70 µm nylon cell strainer (BD Falcon, Bedford, Mass. USA). Cell suspension was spun down (1000×g, 10 minutes), supernatant removed, and cells diluted with DMEM/F12 supplemented with 20% HuS, and 350 µl of cell suspension were put in each well of a four-well sterile plate (day 0).

The cell suspension collected from the pouch of Douglas was also spun down and cells similarly re-suspended and seeded. Cells were incubated at 37° C. and 5% $CO_2$ (Hera-Cell, Haereues, Germany).

After 24 hours (day 1), the medium with unattached cells was collected, and each well gently washed with DMEM/F12 to remove majority of erythrocytes prior to adding new medium with HuS. The collected suspension with unattached cells was spun down, re-suspended in new medium with HuS and seeded in additional new wells. Such cells were assigned as "supernatants," and remaining erythrocytes were similarly washed next day (day 2). The cultures were evaluated daily under the inverted microscope with heated stage (Nikon, Japan).

EXAMPLE 2c

In Vitro Maturation Medium

On day 3 of culture DMEM/F12 medium with HuS in each well was replaced with 350 µl of in vitro Maturation Medium (MediCult IVM, Copenhagen, Denmark) supplemented with FSH and human chorionic gonadotropin (hCG). One ampule of Gonal F (Serono, Switzerland) containing 75 IU (5.5 µg) FSH was first added to 10 ml MediCult IVM medium (FSH solution). One ampule of Pregnyl (Organon, Oss, The Netherlands) containing 5000 IU hCG was also first added to another 10 ml of IVM Medium (hCG solution). Final IVM medium was prepared as 9 ml IVM Medium+1 ml heat inactivated patient's serum+100 µl FSH solution+100 µl hCG solution. The final concentration of hormones was 75 mIU/ml FSH+5 IU/ml hCG.

EXAMPLE 2d

Sperm Preparation and Utilization

On day 3 sperm was prepared on a PureSperm (Nidacon, Goteborg, Sweden) concentration gradient (80% /40%) by centrifugation at 1200 rpm per minute. After that, the 80% fraction with sperm was washed in 5 ml of Sperm Preparation Medium (MediCult, Jyllinge, Denmark) with 50 mM antioxidant hypotaurine and centrifugation at 1400 rpm per minute. The pellet was re-suspended in 0.5 ml Sperm Preparation Medium with hypotaurine. Sperm suspension was left in a $CO_2$-incubator at 37° C. for 30 minutes for "swim-up." Then the aliquot of sperm suspension from the top was taken and 5 drops of sperm suspension were put in each well with ovarian cell culture, except some wells representing controls for comparison of the sperm effect.

EXAMPLE 2e

Evaluation and Freezing of Embryo- and Blastocyst-Like Structures

On days 4-6, the ovarian cell cultures were evaluated for the presence of embryo-, morula, and blastocystlike structures. Several cell stage embryo-like structures, morulae, preblastocyst- and blastocyst-like structures were detected. All these structures were collected and frozen and kept in a liquid nitrogen at −196° C. to be later genetically analyzed and transferred in to the uterus.

EXAMPLE 2f

Immunohistochemistry

The remaining half of each ovarian biopsy was formalin-fixed, embedded in paraffin, and 10 μm sections were collected on microscope slides. Sections were deparaffinized and rehydrated by immersion of slides in the 0.01 M citrate buffer, pH 6.0, at 98° C. for 40 minutes. Slides were then cooled to room temperature, incubated 20 minutes with mouse monoclonal antibody against high molecular weight cytokeratin, clone 34βE12 (Dako, Glostrup, Denmark) diluted 1:200 in phosphate-buffered saline, washed, incubated with peroxidase-coupled rabbit anti-mouse immunoglobulins (Dako), and peroxidase visualized by diaminobenzidine solution as recommended by the vendor (Dako). Finally, the slides were dehydrated and mounted in Canada balsam. The sections were evaluated under the light microscope for the presence of OSE cells and granulosa cells of primary follicles exhibiting brown staining for cytokeratin.

EXAMPLE 2g

Ovarian Surface Epithelium

Staining of biopsy sections for cytokeratin revealed the presence of an OSE layer in ovarian biopsies from Patient 1 and from Patient 3. No OSE was observed in ovarian biopsy from Patient 2. No primary follicles were found in the biopsies from any of the patients.

EXAMPLE 2h

Results of Ovarian Stem Cell Culture

Observations of day 1 revealed sheets of OSE stem cells in Patient 1 and Patient 3 cultures, but no such sheets were observed in cultures from Patient 2. This correlated with the lack of OSE cells in Patient 2 ovarian biopsies and also with the history of autoimmune oophoritis in this patient. In day 2 cultures of Patients 1 and 3, ovarian epithelial cells and fibroblasts attached to the bottom of the dish and very rich ovarian cell cultures developed. Cultures from Patient 2 ovaries showed occasional fibroblasts only.

Primary ovarian cultures exhibited rounded stem cells and fibroblasts. Round oocyte-like cells were observed on day 3 in cultures from Patients 1 and 3, showing germinal vesicle. The most developed oocyte-like cells showed cytoplasmic connection with smaller epithelial cells, which appeared to support the oocyte development by providing additional organelles and then degenerated. Such cells appeared to originate from an incomplete division (lack of separation) of the oocyte precursor, followed by a dominance of one of the divided cells (master and slave principle). In addition, most oocyte-like cells were associated with fibroblasts.

EXAMPLE 2i

Development of Embryo-Like Structures After Fertilization

When sperm were added to the culture, they associated with ovarian cells. This resulted in creation of embryo-like structures in Patients 1 and 3. These structures appeared only in fertilized cultures and not in control dishes without sperm.

In the Patient 1 culture, embryo-like structures appeared in the wells with cells collected from the ovarian surface and pouch of the Douglas, and not in the culture derived from ovarian biopsies, whereas in the Patient 3, the embryo-like structures developed in culture derived from the ovarian biopsy.

Several hours after fertilization of OSE culture on day 3, two-cell structures appeared which resembled two-cell embryos. This phenomenon was observed in cultures from both Patients 1 and 3. On day 4, some four-cell and cleavage stage embryo-like structures were apparent.

On day 5 morula-, preblastocyst- (morulae with early formation of blastocoele), and blastocyst-like structures were observed in the cultures. These embryo-like structures detached spontaneously from the dish bottom and were present in the medium above the attached cells. It was possible to collect them by a sterile glass pipette and to transfer them into the fresh medium for embryo culture.

In Patient 1, there were many (about 20) morula- and preblastocyst-like structures. The morula- and preblastocyst-like structures were smaller than a normal blastocyst and showed no zona pellucida. In Patient 3, only one blastocyst-like structure was found. It had a volume of a normal blastocyst, contained an inner cell mass, trophectoderm, and blastocoele, but showed no zona pellucida, and appeared to hatch during the culture. All collected structures were frozen, each in a separate straw.

Occasionally, parthenogenetically developed morulae were observed, but they appeared earlier (prior to fertilization) than the embryo-like structures developing after fertilization, and they remained attached to the bottom of the dish and surrounded by fibroblasts. During continuation of the culture they did not detach but degenerated.

EXAMPLE 3

Transfer of Embryos Into a Uterus

EXAMPLE 3a

Preparation of Endometrium

In women without menstrual cycles, such as women with POF, endometrial preparation for embryo transfer is modeled on the natural menstrual cycle, using estrogen and progesterone. The initial estrogenic phase is maintained by using daily oral estradiol 4-8 mg. The length of estrogenic exposure is 12-14 days. Progesterone administration follows, 100 mg intramuscularly daily, along with continuation of estrogen supplementation as above. Fresh or frozen-thawed embryos are transferred at the optimal time for embryo transfer, which is 2-4 days after progesterone initiation.

Progesterone (and estrogen) administration are discontinued once the placenta has established adequate steroidogenesis, which occurs at 7-9 week of gestation. Clinically, concentration of serum progesterone is monitored weekly for 10 weeks after embryo transfer, when a serum level of $\geq 30$ ng/ml typically is attained. At that point, supplementation with steroids is terminated.

In patients with a regular menstrual pattern, fresh or frozen-thawed embryos are transferred into the uterus 4 days after the disappearance of the dominant follicle in the natural cycle. Follicular growth monitoring is performed by determination of serum 1 estradiol levels, vaginal ultrasound measurement of follicles and endometrium, and by quick urinary LH determination according to the established protocol for IVF embryo transfer in the natural cycle. After a positive urinary LH and a decrease in estradiol level, the disappearance of the dominant follicle is observed on ultrasound.

In women with irregular menstrual cycles, a minimal stimulation with 75 IU of FSH daily is started on day 7 of the menstrual cycle. When the criteria for follicular maturity are achieved, and if the urinary LH is still negative, ovulation is induced with 5000 IU of hCG, and the transfer of fresh or frozen-thawed embryos is performed 6 days after hCG administration. If the urinary LH is positive, the transfer is performed after the disappearance of the dominant follicle.

EXAMPLE 3b

Transfer of Embryos

Fresh and frozen-thawed embryos are implanted into the uterus using a transfer catheter after endometrium preparation as described above. Frozen embryos are thawed using a two-step thawing protocol with thawing solutions free of cryoprotectant. On the day of transfer, embryos are thawed at room temperature. They are transferred to two thawing solutions free of cryoprotectant glycerol: thawing solution 1 composed of 0.5 M sucrose in the Universal IVF Medium (Medi-Cult, Jyllinge, Denmark) and thawing solution 2 composed of 0.2 M sucrose in the Universal IVF Medium. Embryos are exposed to each solution for 10 minutes at room temperature under a regulated 5% $CO_2$ stream (glass hood). Then they are washed and transferred into the preincubated fresh Universal IVF Medium. One or two embryos are transferred into the uterus about 1 hour after thawing.

Further modifications, uses, and applications of the invention described herein will be apparent to those skilled in the art. It is intended that such modifications be encompassed in the claims that follow.

What is claimed is:

1. A method for obtaining human oocytes comprising culturing in a culture medium ovarian cells including surface epithelial cells and initially containing no oocytes, permitting the cells to remain in the culture medium for a period of time sufficient for the cells to develop into oocytes, and identifying oocytes in the culture, wherein the culture medium contains a source of estrogen.

2. The method of claim 1 wherein the source of estrogen is a chemical compound having estrogenic activity.

3. The method of claim 2 wherein the cells are permitted to remain in the culture medium for at least 4 to 6 days.

4. The method of claim 1 wherein the source of estrogen is from ovarian cells in the culture that produce estrogen.

5. The method of claim 4 wherein the cells are permitted to remain in the culture medium for at least 10 days.

6. The method of claim 1 wherein the ovarian cells that are cultured were obtained from a postmenopausal or anovulatory ovary.

* * * * *